US006358483B1

United States Patent
Trott et al.

(10) Patent No.: US 6,358,483 B1
(45) Date of Patent: Mar. 19, 2002

(54) SPARGER FOR OXYGEN INJECTION INTO A FLUID BED REACTOR

(75) Inventors: Louis Rocco Trott; Robert Angelo Gustaferro, both of Solon; Robert Paul Hepfer, Hudson, all of OH (US); Craig Timothy Miller, Batavia, IL (US); Stig-Axel Carlsson, Solon, OH (US); Benjamin Wayne Close, Aurora, IL (US)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 09/352,465

(22) Filed: Jul. 13, 1999

(51) Int. Cl.[7] .............................. B01F 3/02; B05B 15/00
(52) U.S. Cl. ......................... 422/231; 34/582; 34/585; 239/397.5
(58) Field of Search ................................. 422/231, 143, 422/146; 34/585, 582; 239/397.5, 559, 567

(56) References Cited

U.S. PATENT DOCUMENTS

| 3,460,491 A | * | 8/1969 | Bryk et al. |
| 3,661,165 A | | 5/1972 | Rainbird et al. |
| 3,763,027 A | | 10/1973 | Pearson |
| 3,784,108 A | * | 1/1974 | Hoy et al. ............ 239/226 |
| 3,960,925 A | | 6/1976 | Gasson et al. |
| 4,019,962 A | | 4/1977 | Allen et al. |
| 4,179,071 A | * | 12/1979 | Kozacka ............ 239/397.5 |
| 4,218,407 A | | 8/1980 | Robertson |
| 4,322,384 A | | 3/1982 | Sutton |
| 4,372,825 A | | 2/1983 | Eidschun |
| 4,573,638 A | * | 3/1986 | Junkers ............ 239/397.5 |
| 4,801,731 A | | 1/1989 | Jordan |
| 5,256,810 A | | 10/1993 | Rowe et al. |
| 5,288,473 A | | 2/1994 | Shaw et al. |
| 5,353,319 A | | 10/1994 | Challberg |
| 5,457,223 A | | 10/1995 | Shaw et al. |
| 5,466,857 A | | 11/1995 | Reiling et al. |
| 5,470,149 A | | 11/1995 | Witkowski et al. |
| 5,569,434 A | | 10/1996 | Devanathan et al. |
| 5,676,823 A | | 10/1997 | McKay et al. |
| 5,801,265 A | | 9/1998 | Wagner et al. |

FOREIGN PATENT DOCUMENTS

WO 98/07511 2/1998

OTHER PUBLICATIONS

ASTM Committee G–4 on Compatibility and Sensitivity of Materials in Oxygen Enriched Atmospheres, "Standard Guide for Evaluating Metals for Oxygen Service[1]", Sep. 1992, pp. 971–995.

* cited by examiner

Primary Examiner—Hien Tran
Assistant Examiner—Alexa A. Doroshenk
(74) Attorney, Agent, or Firm—David P. Yusko; Don W. Bulson

(57) ABSTRACT

A sparger includes a conduit for conducting an oxygen feed, a nozzle connected to the conduit for passage of the oxygen feed from the conduit to the outside of the sparger, the nozzle including an orifice and a shroud, and insulation surrounding the conduit and also the shroud substantially the full length of the shroud. A method is provided for producing acrylonitrile via propane ammoxidation, comprising introducing propane and ammonia feeds into a fluid bed of a fluid bed reactor, and introducing an oxygen feed into the fluid bed through at least one insulated and jacketed sparger nozzle for reacting with at least one of the propane feed and ammonia feed in the presence of a fluid bed catalyst.

15 Claims, 3 Drawing Sheets

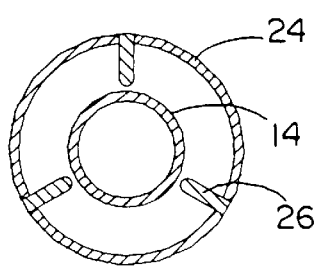
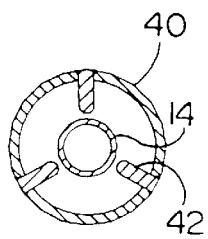
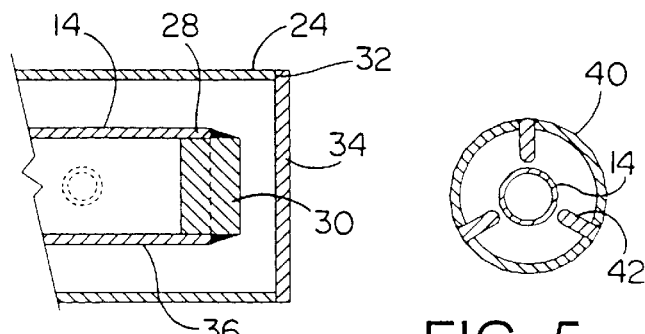
FIG. 3        FIG. 4        FIG. 5
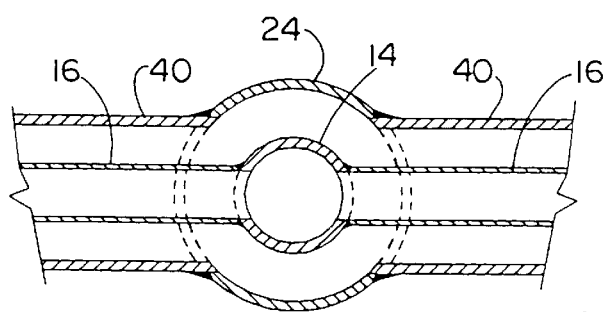
FIG. 6
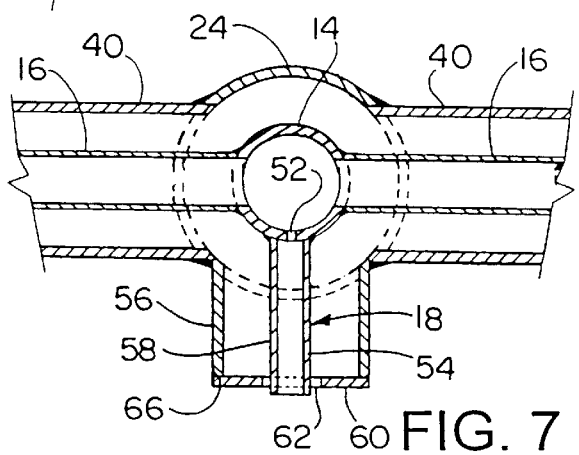
FIG. 7
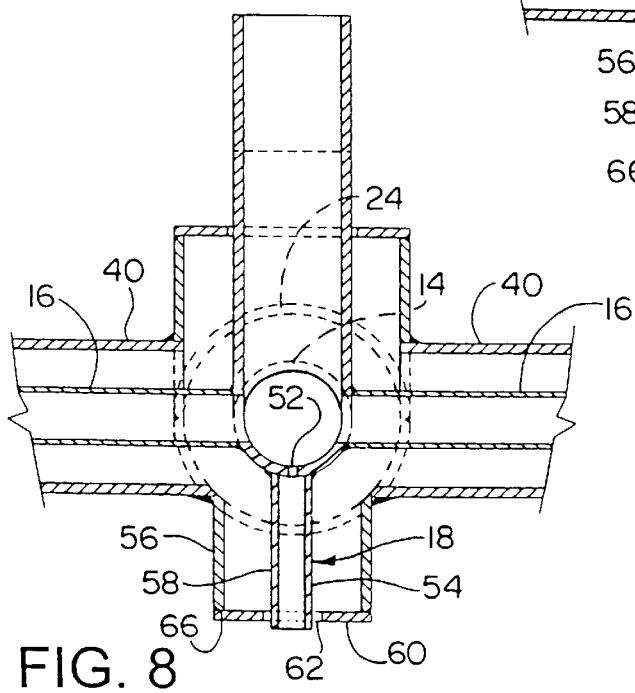
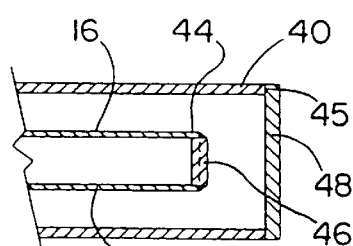
FIG. 8        FIG. 9

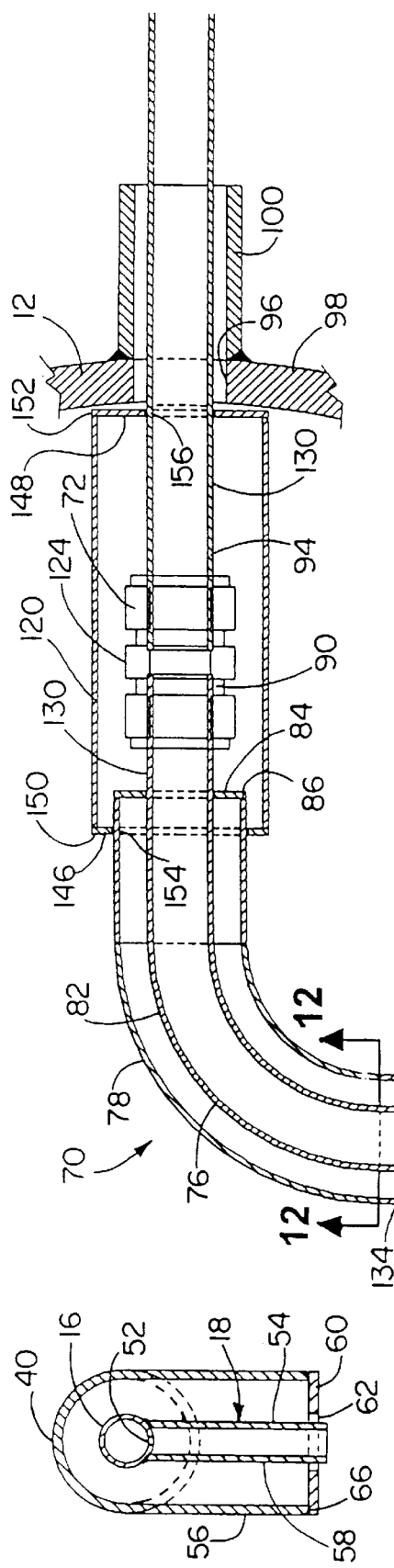
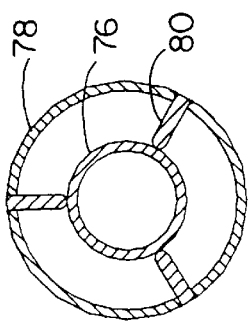
FIG. 12
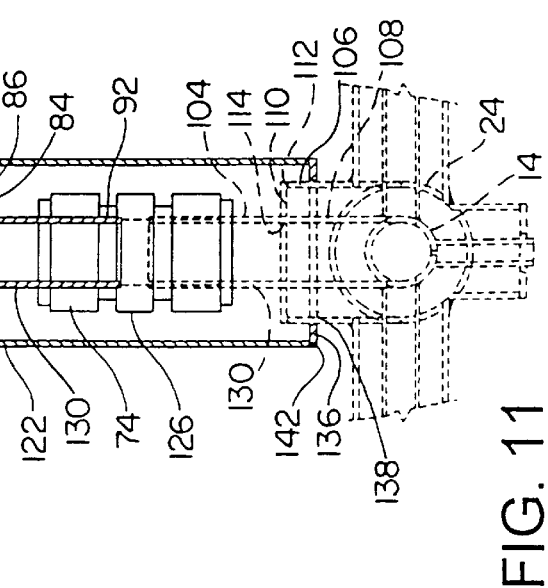
FIG. 10
FIG. 11

SPARGER FOR OXYGEN INJECTION INTO A FLUID BED REACTOR

FIELD OF THE INVENTION

The present invention relates generally to spargers and more particularly to a sparger and method for adding pure oxygen or relatively high concentrations of oxygen directly into a fluid bed reactor.

BACKGROUND

Significant economic advantages can be realized by using pure oxygen instead of air to form acrylonitrile via propane ammoxidation. The ammoxidation process typically consists of reacting propane, ammonia, and air in a fluid bed ammoxidation reactor containing a suitable ammoxidation catalyst to produce acrylonitrile. Also produced are high concentrations of unreacted starting materials, for example, unreacted hydrocarbons and other remaining flammable reactants. These unreacted materials are typically recycled, that is, mixed, in a recycle stream leading back to the fluid bed reactor.

Delivery of an oxygen feed comprising oxygen or high concentrations of oxygen into the fluid bed reactor is challenging because of the sensitivity of working with pure oxygen or oxygen-rich streams. By using an oxygen feed instead of an air feed, flammability envelopes are widened and oxidation reactions are accelerated.

Typically, one or more spargers are incorporated into the fluid bed reactor vessel for delivering into the interior thereof and agitating therein the reactants of the ammoxidation process. During a propane ammoxidation process, temperatures may vary within the reactor vessel from about 400 to 500° C. and, accordingly, spargers disposed within the reactor vessel will likewise vary in temperature as will the reactants carried by the sparger. As the temperature of a conventional sparger increases with increased reactor temperature, the flammability of a combustible material in the presence of an oxygen feed delivered therethrough would increase. As a consequence, spargers could exhibit undesirable burning because of their increased likelihood to ignite within the widened oxygen flammability limits. For example, spargers made of ordinary metals like carbon steels or even stainless steels, if used to inject pure oxygen or relatively high concentrations of oxygen, may ignite and locally burn inside a fluid bed reactor vessel for propane ammoxidation.

SUMMARY OF THE INVENTION

The present invention provides a sparger and method for injecting an oxygen feed into a fluid bed reactor. The sparger and method have particular application for injecting an oxygen feed into a fluid bed catalytic reactor for the ammoxidation of a propane feed and an ammonia feed. The oxygen feed may be oxygen enriched air (greater than 21% oxygen), pure oxygen (100% oxygen) or a high concentration of oxygen (greater than 50% oxygen). Other representative processes in which principles of the instant invention may be employed are the catalytic cracking of oils to produce gasoline and other light hydrocarbons, the coking of residua, coke gasification, the oxidation of benzene or n-butane or maleic anhydride, the ammoxidation of propylene to acrylonitrile, and the oxidation of hydrogen chloride to chlorine.

According to one aspect of the invention, the sparger and method are characterized by a feed conduit for conducting the oxygen feed and a nozzle connected to the feed conduit for passage of the oxygen feed from the feed conduit to outside the sparger. The nozzle includes an orifice and a shroud, and insulation surrounds the conduit and also surrounds the shroud substantially the full length of the shroud. In a preferred embodiment, a conduit jacket surrounds the conduit and a shroud jacket surrounds the shroud, and insulation is interposed between the conduit and conduit jacket and between the shroud and he shroud jacket. Also in a preferred embodiment, the shroud jacket terminates at a cheek plate at least partially closing an outer end of an annular space between the shroud and shroud jacket, which cheek plate closely surrounds the shroud but is radially spaced apart from the shroud by an amount sufficient to allow for differential expansion.

According to another aspect of the invention, a fluid bed reactor comprises a reactor vessel for containing a fluid bed and a sparger disposed within the reactor vessel for delivery of an oxygen feed into the fluid bed. The sparger includes at least one nozzle for directing a stream of the oxygen feed into the fluid bed. The nozzle is at least partially thermally insulated for inhibiting heat transfer from the interior of the reactor to the interior of the nozzle in order to maintain, at a fluid bed temperature greater than about 400° C., the temperature of the oxygen feed below a temperature at which the materials of construction of the nozzle (or any combustible impurities therein) would ignite.

According to yet another aspect of the invention, a method is provided for introducing an oxygen feed into a fluid bed maintained at a temperature of about 400° C. or higher, the method comprising the use of a sparger disposed within the fluid bed for introducing the oxygen feed into the fluid bed through at least one sparger nozzle.

According to a further aspect of the invention, a method is provided for the production of acrylonitrile via propane ammoxidation comprising the steps of introducing propane and ammonia into a fluid bed reactor, introducing an oxygen feed into the fluid bed reactor through a sparger to react the propane, ammonia and oxygen feed in the presence of a fluid bed catalyst to produce the corresponding acrylonitrile, and maintaining the temperature of the oxygen feed while inside the sparger below the temperature at which the materials of construction of the sparger (or any combustible impurities therein) would ignite.

The foregoing and other features of the invention are hereinafter fully described and particularly pointed out in the claims, the following description and the annexed drawings setting forth in detail one or more illustrative embodiments of the invention, such being indicative, however, of but one or a few of the various ways in which the principles of the invention may be employed.

BRIEF DESCRIPTION OF THE DRAWINGS

FIG. 3 is a cross-sectional view of a header pipe of the sparger as viewed from the plane 3—3 in FIG. 2.

FIG. 4 is a partial cross-sectional view of an end of the header pipe as viewed from the plane 4—4 in FIG. 2.

FIG. 5 is a cross-sectional view of a lateral pipe of the sparger as viewed from the plane 5—5 in FIG. 2.

FIG. 6 is a partial cross-sectional view of a portion of the sparger where the header pipe and lateral pipe intersect as viewed from the plane 6—6 in FIG. 2.

FIG. 7 is a partial cross-sectional view of a portion of the sparger where the header pipe, a lateral pipe and a nozzle intersect as viewed from the plane 7—7 in FIG. 2.

FIG. 8 is a cross-sectional view of a portion of the sparger where the header pipe, a lateral pipe, a nozzle and the feed line intersect as viewed from the plane 8—8 in FIG. 2.

FIG. 9 is a partial cross-sectional view of an end of a lateral pipe of the sparger as viewed from the plane 9—9 in FIG. 2.

FIG. 10 is a cross-sectional view of a nozzle extending from a lateral pipe of the sparger as viewed from the plane 10—10 in FIG. 2.

FIG. 11 is a cross-sectional view of a feed line for the sparger.

FIG. 12 is a cross-sectional view of the feed line as viewed from the plane 12—12 in FIG. 11.

DETAILED DESCRIPTION

Figure 1:
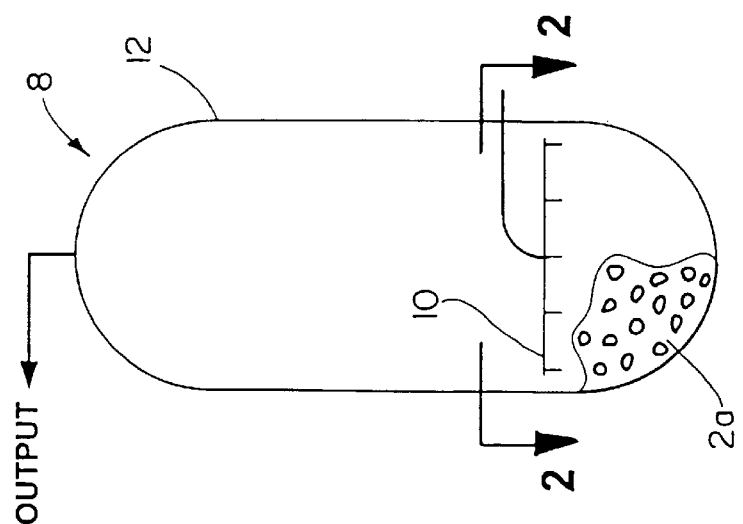
FIG. 1 is a simplified schematic cross-sectional illustration of a fluid bed reactor including a sparger constructed in accordance with the invention.

Referring now in detail to the drawings and initially to FIG. 1, a fluid bed reactor is designated generally by reference number 8. The fluid bed reactor 8 includes a reaction or reactor vessel 12 in which a gas-solid or liquid-solid contacting process occurs. In the reactor, a bed of finely divided solid particles (e.g. a fluid bed catalyst) is lifted and separated by using a stream of process gas or liquid. Fluid bed reactors exist in all shapes and sizes. Typically the reactors are equipped with a grid near the bottom of the reactor which supports a catalyst bed while allowing process feed to pass through. The remainder of this description focuses in the practice of the instant invention in gas-solid contacting processes and particularly an ammoxidation process that typically consists of reacting propane, ammonia, and a source of oxygen in the reactor containing a suitable ammoxidation catalyst to produce acrylonitrile. However, the apparatus and methods described herein are equally applicable to other processes, including liquid-solid contacting processes.

Figure 2:
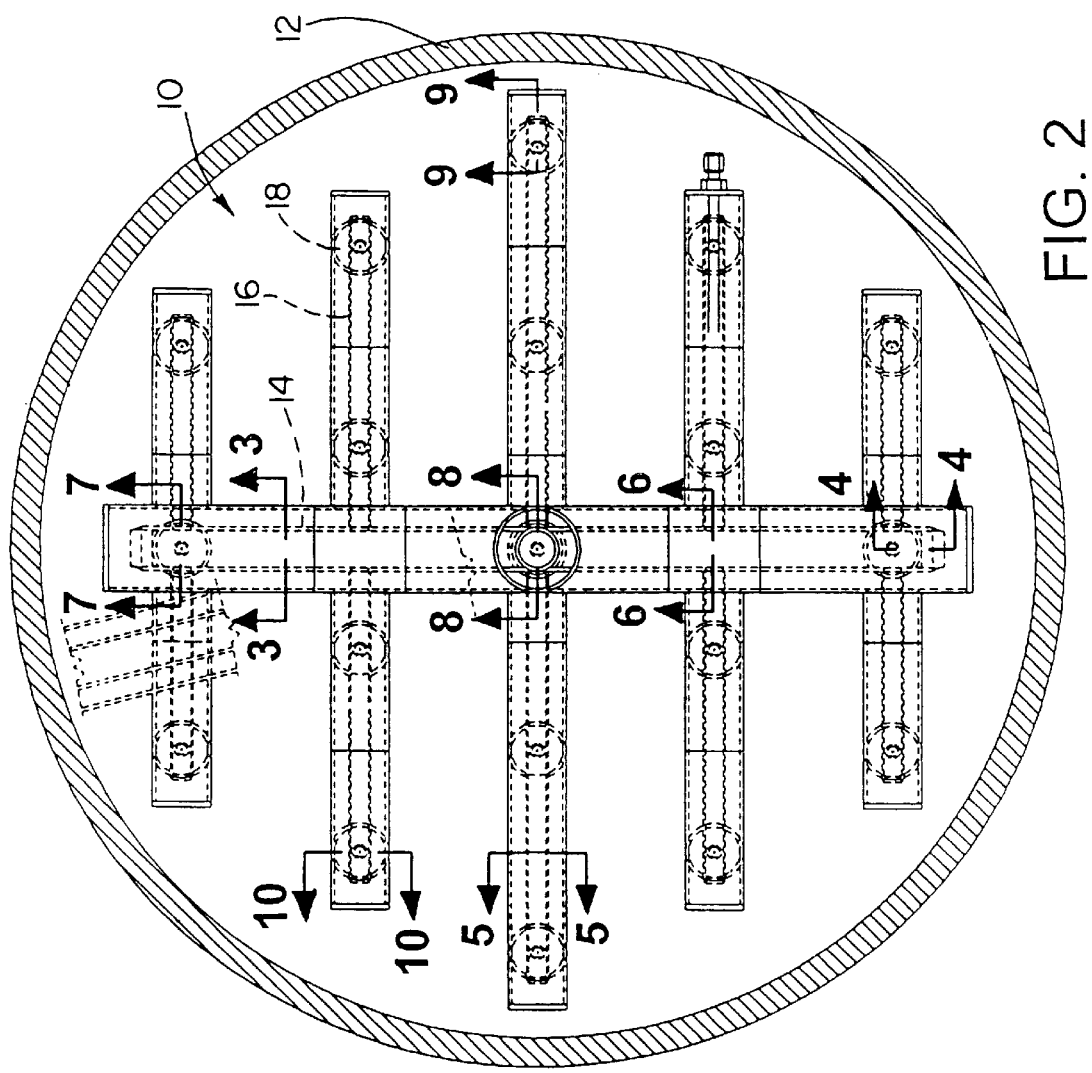
FIG. 2 is a cross-sectional view of the fluid bed reactor as viewed from the plane 2—2 in FIG. 1.

With additional reference to FIG. 2, the reactor vessel 12 has disposed therein, for delivery of an oxygen feed, an exemplary sparger 10 constructed in accordance with the present invention. The sparger 10 generally includes a header pipe 14, one or more lateral pipes 16 and one or more nozzles 18, all of which are thermally insulated and are preferably made of metals that have high resistance to burning in oxygen. The lateral pipes 16 extend transversely outwardly from the header pipe 14. That is, the lateral pipes 16 extend in a perpendicular, or T-shaped, relation to the header pipe 14. The nozzles preferably are positioned along the lengths of the header and lateral pipes in a triangular-like pattern (or pitch) for uniform distribution of the oxygen feed across the cross-section of the vessel, although other nozzle and/or pipe configurations may be employed.

During the process of manufacture of acrylonitrile, an oxygen feed is fed through the header pipe 14 into the lateral pipes 16 for dispersion through the nozzles 18 into a fluid bed catalyst 20 contained in the reactor vessel 12. As used herein, an oxygen feed is a feed having an oxygen concentration higher than the normal percentage concentration of oxygen in air, such as, oxygen enriched air (greater than 21% oxygen), pure oxygen (100% oxygen) or a high concentration of oxygen (greater than 50% oxygen). The oxygen feed is mixed with propane and ammonia feeds delivered by any suitable means (not shown). For example, the ammonia feed may be delivered by a similar sparger upstream, downstream or at the same level as the oxygen sparger, and the propane feed may be introduced via an inlet at the upstream end of the vessel 12. Together, the propane, ammonia and oxygen feeds react to produce acrylonitrile.

The hereinafter described construction of the sparger 10 maintains the temperature of the oxygen feed passing through the sparger 10 at a temperature below which the metal of the pipes 14 and 16 and particularly the nozzles 18 would ignite. These and other advantages, as well as the structure, function, and other features of the invention are described in greater detail below.

As shown in FIG. 3, the header pipe 14 is surrounded by a conduit jacket 24 spaced apart from the header pipe 14 by spacers 26. The spacers 26, which may be three equally circumferentially spaced apart pins or ribs having rounded ends, maintain the header pipe 14 centered in and thus concentric with the conduit jacket 24. The spacers 26 are located along the length of the header pipe, for example at locations midway between the connections of the header pipe 14 with the lateral pipes 16. As shown in FIG. 4, the header pipe 14 is closed at its ends 28 preferably by end plugs 30 inserted therein and welded thereto. The conduit jacket 24 is also closed at its ends 32 preferably by plate discs 34 welded thereto. The annular space between the header pipe 14 and conduit jacket 24 is filled with thermal insulation to cover the exterior surface 36 of the header pipe 14. A preferred insulation is a ceramic paper insulation.

Like the configuration of the header pipe 14, the lateral pipes 16 are surrounded by respective conduit jackets 40 spaced apart from the lateral pipes 16 by spacers 42 as seen in FIG. 5. The spacers 42, which may be three equally circumferentially spaced apart pins or ribs having rounded ends, maintain the lateral pipes 16 centered and thus concentric with the respective conduit jackets 40. The spacers 42 are located along the length of each lateral pipe, for example at locations approximately midway between the connections of the lateral pipe and nozzles 18.

As shown in FIGS. 6–9, the lateral pipes 16 and lateral conduit jackets 40 are sealingly connected, preferably by welding, to the header pipe 14 and header conduit jacket 24, respectively. The lateral pipes 16 and conduit jackets 40, similar to the header pipe 14 and conduit jacket 24, are closed at their distal ends 44 and 45 by end plugs 46 and plate discs 48, respectively. The annular space between the lateral pipes 16 and conduit jackets 40 are filled with thermal insulation to cover the exterior surface 50 of the lateral pipes 16. Again, a preferred insulation is a ceramic paper insulation.

As seen in FIGS. 7, 8 and 10, each nozzle 18 includes an orifice 52. The orifices of the nozzles are configured preferably to provide for even distribution of the oxygen feed transversely across the fluid bed reactor 12. As above noted, the nozzles, and thus the orifices, are arranged in a triangular pattern (FIG. 2). That is, the orifices are equidistant from one another and form a repeated pattern across the sparger 10. For example, any three neighboring orifices 52 form an equilateral triangle of the same size as an adjacent equilateral triangle formed by another three neighboring orifices 52. The orifices 52 are sized to provide a desired pressure drop and flow velocity that prevents or substantially reduces the probability of backflow of any reactant gases into the header pipe 14 or the lateral pipes 16.

Each nozzle 18 includes a protective shroud 54 for directing the oxygen feed into the fluid bed catalyst 20 contained in the reactor vessel 12 (FIG. 1). In the illustrated embodiment, each protective shroud 54 extends downwardly from, and are sealingly connected to, preferably by welding, the header pipe 14 (FIGS. 7 and 8) or the lateral pipes 16 (FIG. 10).

In accordance with the invention, shroud jackets 56 surround the shrouds. The shroud jackets are spaced apart from the respective shrouds 54 and are connected to the corresponding conduit jackets 24, 40 of the header pipe 14 or lateral pipe 16, preferably by welding. The annular space between the shrouds 54 and shroud jackets 56 is filled with thermal insulation, preferably a ceramic paper insulation, to cover the exterior surface 58 of the shrouds 54.

The ends of the shroud jackets 56 are substantially closed by cheek plates 60. The cheek plates 60 are connected to the respective bottom ends 66 of the shroud jackets 56 and have a center opening 62, or aperture, through which the protective shrouds 54 extend. The openings 62 are sized larger than the diameters of the shrouds 54 to enable the cheek plates 60 and shrouds 54 to expand and/or contract relative to one another. The cheek plates 60 retain and protect the thermal insulation within the annular space between the shrouds 54 and shroud jackets 56. As is preferred, the shrouds extend only a short distance beyond the respective cheek plates as shown.

Referring now to FIG. 11, an oxygen feed line is generally indicated by reference numeral 70. The feed line 70 is connected to and in fluid communication with the sparger 10 at the header pipe 14. In the illustrated embodiment, the feed line 70 generally includes tube couplings 72 and 74 respectively connecting opposite ends 90 and 92 of an elbow pipe 76 to an oxygen feed source conduit 94 and a transition conduit 104. However, other means, such as welding, may be used to connect the elbow pipe to the conduits 94 and 104. Like the header pipe 14, lateral pipes 16 and nozzles 18, the elbow pipe 76 is surrounded by a jacket 78 spaced apart from the elbow pipe 76. Spacers 80 (FIG. 12) maintain the annular space between the elbow pipe 76 and conduit jacket 78. The annular space is filled with thermal insulation, preferably a ceramic paper insulation, to cover the exterior surface 82 of the elbow pipe 76. Cheek plates 84 are connected to the respective ends 86 of the conduit jacket 78.

The oxygen feed source conduit 94 extends through an opening 96 in a side wall 98 of the reactor vessel 12. A penetration coupling 100 connected to the reactor vessel wall 98 surrounds the oxygen feed source conduit 94 for protection. The transition conduit 104 is sealingly connected, preferably by welding, to the header pipe 14. The transition conduit 104 is disposed in and spaced apart from a conduit jacket 106 that is connected to the conduit jacket 24 surrounding the header pipe 14, preferably by welding. The transition conduit 104 and conduit jacket 106 form an annular space therebetween in which thermal insulation, preferably a ceramic paper insulation, is filled to cover the exterior surface 108 of the transition conduit 104. A plate disc 110 is connected to the end 112 of the conduit jacket 106. The plate disc 110 has an opening 114 through which the transition conduit 104 extends.

The tube couplings 72 and 74 are disposed in respective outer casings 120 and 122. The spaces within the casings 120 and 122 and around the tube couplings 72 and 74 are filled with thermal insulation, preferably a ceramic paper insulation, to cover the exterior surfaces 124 and 126 of the tube couplings 72 and 74, as well as portions 130 of the transition conduit 104, elbow pipe 76 and oxygen feed source conduit 94. The casing 122 includes a cheek plate 132 that has an opening 134 through which the elbow pipe 76 extends. The casing also includes a cheek plate 136 that has an opening 138 through which the transition conduit 104 and conduit jacket 106 extend. The cheek plates 132 and 136 are preferably welded to the respective ends 140 and 142 of the outer casing 122 and are operative to maintain the thermal insulation in the annular space. The casing 120 also has cheek plates 146 and 148 connected at its ends 150 and 152, preferably by welding. The cheek plate 146 has an opening 154 through which the elbow pipe 76 extends. Likewise, the cheek plate 136 has an opening 156 through which the oxygen feed source conduit 94 extends.

In view of the foregoing, it will be appreciated that the sparger 10, as well as the oxygen feed line 70 connected to the sparger 10, are substantially entirely surrounded by thermal insulation. The insulation, in turn, is substantially entirely covered by the spaced apart conduit jackets and shroud jackets to stabilize and protect the insulation. The size of the spacing and the corresponding type and amount of insulation depends on such factors as the size and configuration of the reactor vessel, the inlet temperatures and flow rates of the ammonia feed, propane feed and oxygen feed, and the metal of which the sparger 10 and reactor 12 are constructed.

The thermal insulation blocks heat transfer, or substantially reduces the rate of heat transfer, from the interior of the reactor vessel 12. As a result, the temperature of the oxygen feed is maintained below a temperature that prevents the header pipe 14, lateral pipes 16 and shrouds 54 of the sparger 10, or contaminants that may be in the stream of oxygen feed communicated therethrough, from igniting. In particular, because the insulation surrounding the shrouds 54 extends substantially the full length of the shrouds 54, there is less likely a chance of premature or undesirable oxidation reactions from developing near the ends of the shrouds 54.

To further reduce the chance of ignition of the sparger 10, the header pipe 14, lateral pipes 16, and shrouds 54 are constructed of metals that have high resistance to combustion with the oxygen feed. Preferred metals include nickel and copper alloys, for example, nickel 200 or Monel 400, although other metals such as stainless steel may also be used.

During the process of manufacture of acrylonitrile, the reactants, i.e., an ammonia feed and propane feed, are fed into the fluid bed reactor 12, which contains the fluid bed catalyst 20, via a sparger or other delivery apparatus (not shown) upstream, downstream or at the same elevation as the oxygen feed sparger 10. An oxygen feed, in the form of pure oxygen or a mixture containing a high concentration of oxygen, is fed through the oxygen feed sparger 10 for dispersion directly into the fluid bed catalyst 20. The catalyst 20 in the path of the nozzle outlet streams is preferably comprised of finely divided catalyst solids, for example having an average particle size of 50 microns, that assists in resisting or retarding the formation or propagation of flames. The shrouds 54 are sized to maintain a gas jetting velocity, for example between 20–30 feet/sec, into the fluid bed reactor 12 without substantial attrition of the catalyst contained therein. The fluid bed pressure may by example be about 15–17 psig and at a temperature of about 490–500° C.

A model of the sparger 10 was constructed in accordance with the invention and, as illustrated in the Figures, includes the header pipe 14, which communicates the oxygen feed to ten outwardly extending spaced apart lateral pipes 16. The header pipe 14 or lateral pipes 16 communicate the oxygen feed to 19 nozzles which include the orifices 52 and shrouds 54 that extend downwardly (into the paper in FIG. 2) from the header pipe 14 or lateral pipes 16. The feed line 70 is centrally disposed relative to the orifices 52 and are configured so as to distribute the oxygen feed uniformly across the fluid bed reactor 12.

Tests conducted with such model have shown that with a fluid bed reactor temperature in the range of about 400 to about 500° C., the temperature of the oxygen feed can be maintained at about 90 to about 120° C. (as estimated by standard heat transfer calculations). The orifices were sized to maintain a velocity in the range of about 400 to about 600 ft/sec at the orifice and the shrouds were sized to attain a gas jetting velocity in the range of about 20 to about 30 ft/sec, with a fluid bed pressure of about 15–17 psig.

Although the invention has been shown and described with respect to certain preferred embodiments, equivalent alterations and modifications will occur to others skilled in the art upon reading and understanding this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiment or embodiments of the invention. In addition, while a particular feature of the invention may have been described above with respect to only one of several illustrated embodiments, such feature may be combined with one or more other features of the other embodiments, as may be desired and advantageous for any given or particular application.

What is claimed is:

1. A sparger for injecting an oxygen feed into a fluid bed reactor, comprising:
    a conduit for conducting the oxygen feed,
    a nozzle connected to the conduit for passage of the oxygen feed from the conduit to outside the sparger, the nozzle including an orifice and a shroud,
    insulation surrounding the conduit and also the shroud substantially the length of the shroud,
    a conduit jacket surrounding the conduit, and
    a shroud jacket surrounding the shroud, and
    wherein the insulation is interposed between the conduit and conduit jacket and between the shroud and the shroud jacket, and wherein said shroud jacket terminates at a cheek plate at least partially closing an outer end of an annular space between the shroud and shroud jacket.

2. A sparger as set forth in claim 1, wherein the shroud has a cross-sectional area greater than the cross-sectional area of the orifice.

3. A sparger as set forth in claim 1, wherein the cheek plate has a central annular edge spaced radially outwardly of the shroud, whereby the shroud and cheek plate can differentially expand while the cheek plate functions to retain the insulation interiorly thereof.

4. A fluid bed reactor comprising a reactor vessel for containing a fluid bed, and the sparger of claim 3 extending within the reactor vessel.

5. A sparger for injecting oxygen feed into a fluid bed reactor comprising:
    a header pipe for communicating oxygen feed into an interior region of a fluid bed reactor operating at a reactor temperature;
    at least one lateral pipe extending from and in fluid communication with said header pipe;
    at least one nozzle extending from and in fluid communication with either said header pipe or said lateral pipe and in fluid communication with the fluid bed reactor;
    the header pipe, lateral pipe, and nozzle being operative to inject the oxygen feed into the reactor and being at least partially thermally insulated at their exterior surfaces for inhibiting heat transfer from the interior of the reactor to the respective interiors of the header pipe, lateral pipe and nozzle, in order to maintain, at a fluid bed temperature greater than about 400 C, the temperature of the oxygen feed below a temperature at which the materials of construction of the header pipe, lateral pipe, and nozzle would ignite; and
    wherein the nozzle includes an orifice and a shroud having a cross-sectional area greater than the cross-sectional area of the orifice, insulation surrounds the shroud substantially the length of the shroud, a shroud jacket surrounds the shroud, with insulation interposed between the shroud and the shroud jacket, and wherein said shroud jacket terminates at a cheek plate at least partially closing an outer end of an annular space between the shroud and shroud jacket.

6. A sparger as set forth in claim 5, wherein the header pipe, lateral pipe, and nozzle are at least partially thermally insulated at their exterior surfaces for maintaining the temperature of the oxygen feed at a temperature less than about 150° C.

7. A sparger as set forth in claim 5, wherein the thermal insulation comprises a ceramic paper material.

8. A sparger as set forth in claim 5, wherein a jacket is provided about the outside surface of the thermal insulation to provide a protective surface for the insulation.

9. A sparger as set forth in claim 5, wherein at least one of the header pipe, lateral pipe, or nozzle are constructed of a material that is resistant to combustion with oxygen.

10. A sparger as set forth in claim 9, wherein at least one of the header pipe, lateral pipe, or nozzle are constructed of Monel 400 or Nickel 200.

11. A fluid bed reactor comprising a reactor vessel for containing a fluid bed, and the sparger of claim 5 extending within the reactor vessel.

12. A fluid bed reactor as set forth in claim 11, including a fluid bed catalyst in the reactor vessel.

13. A fluid bed reactor as set forth in claim 12, wherein the shroud is sized to attain a gas jetting velocity of about 20 to about 30 feet per second.

14. A fluid bed reactor as set forth in claim 12, further comprising a feed line that penetrates a wall of the reactor for communicating oxygen feed from the exterior of the reactor to the header pipe.

15. A fluid bed reactor as set forth in claim 12, further comprising a feed line that penetrates a wall of the reactor for communicating oxygen feed from the exterior of the reactor to the header pipe and wherein the at least one nozzle comprises a plurality of nozzles including respective orifices, the feed line being centrally disposed relative to the nozzles and the orifices being configured to distribute the oxygen feed uniformly throughout the reactor.

* * * * *